United States Patent
Humar et al.

(10) Patent No.: US 9,149,460 B2
(45) Date of Patent: Oct. 6, 2015

(54) COATED PARTICLES AND PHARMACEUTICAL DOSAGE FORMS

(75) Inventors: Vlasta Humar, Stahovica (SI); Mateja Burjak, Vrhnika (SI); Rok Grahek, Kranj (SI); Mateja Salobir, Ljubljana (SI); Janez Kerc, Ljubljana (SI); Klemen Kocevar, Vrhnika (SI)

(73) Assignee: Lek Pharmaceuticals d.d. (SI)

( * ) Notice: Subject to any disclaimer, the term of this patent is extended or adjusted under 35 U.S.C. 154(b) by 868 days.

(21) Appl. No.: 11/862,470

(22) Filed: Sep. 27, 2007

(65) Prior Publication Data

US 2008/0138429 A1 Jun. 12, 2008

Related U.S. Application Data

(63) Continuation of application No. 10/544,920, filed as application No. PCT/SI2004/000009 on Feb. 11, 2004, now abandoned.

(30) Foreign Application Priority Data

Feb. 12, 2003 (SI) .................................. P200300041

(51) Int. Cl.
| | | |
|---|---|---|
| A61K 9/24 | (2006.01) | |
| A61K 31/225 | (2006.01) | |
| A61K 31/40 | (2006.01) | |
| A61K 9/20 | (2006.01) | |
| A61K 9/28 | (2006.01) | |

(52) U.S. Cl.
CPC ............... *A61K 31/40* (2013.01); *A61K 9/2009* (2013.01); *A61K 9/2018* (2013.01); *A61K 9/2054* (2013.01); *A61K 9/2866* (2013.01)

(58) Field of Classification Search
CPC .......... A61K 9/24; A61K 31/225; A61K 9/14
USPC .................. 424/422, 433–440, 464, 472–480
See application file for complete search history.

(56) References Cited

U.S. PATENT DOCUMENTS

| 6,210,712 B1 * | 4/2001 | Edgren et al. ................. 424/473 |
| 6,248,363 B1 * | 6/2001 | Patel et al. .................... 424/497 |
| 6,706,283 B1 * | 3/2004 | Appel et al. .................. 424/473 |
| 2004/0138290 A1 * | 7/2004 | Kerc et al. ..................... 514/423 |

FOREIGN PATENT DOCUMENTS

| WO | 96/01874 | | 1/1996 |
| WO | WO 99/06035 | * | 2/1999 |
| WO | 01/04195 A1 | | 1/2001 |
| WO | 01/54668 A1 | | 8/2001 |
| WO | 01/54669 A1 | | 8/2001 |
| WO | 99/06035 | | 2/2009 |

OTHER PUBLICATIONS

Third Party Observations according to Art 115 EPC concerning the European patent application EP 04 710 142. Mar. 12 19 (EP 1 594 474) filed in the name of Lek Pharmaceuticals d.d.

* cited by examiner

*Primary Examiner* — Michael G Hartley
*Assistant Examiner* — Jagadishwar R Samala
(74) *Attorney, Agent, or Firm* — Luedeka Neely Group, P.C.

(57) ABSTRACT

The present invention relates to coated particles and pharmaceutical dosage forms comprising the active substances sensitive to environmental influences. The coating of the present invention provides stability and protection of the active substance to environmental influences and in particular from oxidation and/or environmental humidity by coating.

20 Claims, No Drawings

COATED PARTICLES AND PHARMACEUTICAL DOSAGE FORMS

This application is a continuation of application Ser. No. 10/544,920, filed Nov. 4, 2005 now abandoned, which is a 371 National Phase Entry of PCT Application PCT/SI04/00009, filed Feb. 11, 2004, which in turn claims priority to Slovenian patent application P-200300041, filed Feb. 12, 2003.

FIELD OF THE INVENTION

The present invention relates to the field of pharmaceutical industry, more specifically to coated particles and pharmaceutical dosage forms comprising the active substances sensitive to environmental influences.

The coated particles of the present invention are the particles of the active substance or the particles of the active substance and one or more pharmaceutical excipients in the form of particles of regular or irregular shapes, such as microcapsules, microspheres, granules, pellets and the like said particles are protected from environmental influences and in particular from oxidation and/or environmental humidity by coating. Said particles are embedded either in an uncoated pharmaceutical dosage form or in a coated pharmaceutical dosage form wherein the coating of the present invention affords protection and consequently stability of the active substance and one or more pharmaceutical excipients from environmental influences and in particular from oxidation and/or environmental humidity. When coated particles are embedded in a coated pharmaceutical dosage form said coating could be also any other in the prior art known coating.

The pharmaceutical dosage forms of the present invention are the uncoated or coated pharmaceutical dosage forms.

The uncoated pharmaceutical dosage forms of the present invention comprise the coated particles of the present invention and one or more pharmaceutical excipients wherein the coating of such particles affords protection of the active substance and one or more pharmaceutical excipients from environmental influences and in particular from oxidation and/or environmental humidity.

The coated pharmaceutical dosage forms of the present invention comprise coated particles of the present invention and/or uncoated particles of the active substance or of the active substance and one or more pharmaceutical excipients and the coating which affords protection of the active substance and one or more pharmaceutical excepients from environmental influences and in particular from oxidation and/or environmental humidity. When coated particles are embedded in a coated pharmaceutical dosage form said coating could be also any other in the prior art known coating.

The coated particles and the pharmaceutical dosage forms of the present invention are stable to the influences of the environment, that is, afford stability of the active substance, which is sensitive to environmental influences, and one or more pharmaceutical excipients to environmental influences by protecting the active substance and one or more pharmaceutical excipients from environmental influences and in particular from oxidation and/or environmental humidity.

The present invention also relates to the coated particles and the pharmaceutical dosage forms comprising the active substance which is HMG-CoA reductase inhibitor.

The present invention also relates to the methods and the processes for the preparation of the coated particles and the pharmaceutical dosage forms of the present invention.

The present invention further relates to the use of the active substance for the preparation of the coated particles and/or pharmaceutical dosage forms of said invention for the treatment and to the methods of treatment for a variety of diseases by administering the coated particles and/or pharmaceutical dosage forms of the present invention wherein the diseases are selected from the group consisting of dyslipidemia, hyperlipidemia, hypercholesterolemia, atherosclerosis, arteriosclerosis, cardiovascular disease, coronary arterial disease, coronary heart disease, vascular disorders, inflammatory disease, allergic disease, neurodegenerative disease, cancer disease, viral disease (WO 0158443), abnormal bone states, (WO 0137876), amyloid-(precursor protein processing disorders such as Alzheimer's disease or Down's Syndrome (WO 0132161).

BACKGROUND OF THE INVENTION

Many therapeutic substances are sensitive to environmental influences and due to these impacts their active forms are transformed to degradation products which are often less effective than the active forms. Apart from lower efficacy, degradation products may also cause undesirable effects thus affecting safe use of a medicament. Already a very low percent of impurities or degradation products of the active substance may significantly impair a drug safety. Therefore, it is important that therapeutic substance is as pure as possible when administered, that is, the percent of degradation products and impurities should be minimal.

Procedures for the preparation of an active substance per se (e.g., processes of isolation and purification), and interim phases of storage of the active substance and/or its intermediates during the production and the phases of storage of the active substance up to the procedure and during the course of pharmaceutical dosage form production have an influence on the percent of impurities and degradation products of the active substance. At the same time, pharmaceutical excipients comprised in the pharmaceutical dosage form have an influence on the percent of degradation products and impurities in the active substance. Said pharmaceutical excipients are selected from the group consisting of fillers or diluents, binders, lubricants, glidants, disintegrants, colorants, flavors, adsorbents, plasticizers and the like.

Not only an active substance undergoes degradation by environmental influences but also excipients in a pharmaceutical dosage form may be degraded. Degradation products of the latter act as the reactive sites which trigger degradation reactions of the active substance in a pharmaceutical dosage form.

Among the environmental factors which have an impact on an active substance are, for example, temperature, humidity, light, (e.g. UV light) and gases, present in the environment such as, e.g., oxygen or carbon dioxide. An important factor is also the pH environment, that is, presence of substances which have influence on acidity or alkalinity of the environment (e.g., acids, alkalis, salts, metal oxides) and the reactivity of the ambient medium or active substance (free radicals, heavy metals), etc.

The majority of therapeutic active substances are sensitive to temperature, in particular high temperature. Temperature increase accelerates chemical reactions and thus more degradation products are formed in a shorter period of time. In certain cases at elevated temperature the reactions take place which would not at normal temperature. Thus, the temperature has an impact on the kinetic and thermodynamic parameters of the chemical reactions leading to occurrence of degradation products.

Many active substances are sensitive to humidity. At increased humidity water is bound to the active substance itself and/or pharmaceutical excipients surrounding the active substance. Water associated with one or more other environmental influences may thus triggers degradation reactions of the active substance. For example, substances known in the prior art to be sensitive to humidity are:

β-lactamase inhibitor potassium clavulanate (Finn, M. J. et al, J. Chem. soc. Perkin. Trans 1, 1984, 1345-349; Haginaka J. et al, Chem. Pharm. Bull. 29, 1981, 3334-3341; Haginaka J. et al, Chem. Pharm. Bull. 33, 1985, 218-224);

proton pump inhibitors such as, e.g. omeprazole, lansoprazole and pantoprazole (Kristi, A. et al, Drug. Dev. Ind. Pharm. 26 (7), 2000, 781-783; Ekpe, A. et al, Drug. Dev. Ind. Pharm. 25 (9), 1999, 1057-065);

HGM-CoA reductase inhibitors, e.g. pravastatin and atorvastatin.

Compounds containing structural elements which at low pH are converted to a lactone form are generally sensitive to an acidic environment. Among them the best known are HGM-CoA reductase inhibitors (statins) and related compounds which comprise 7-substituted-3,5-dihydroxyheptanoic and/or 7-substituted-3,5-dihydroxyheptenoic acid groups. Apart from conversion to a lactone form, other mechanisms of degradation of said active substances may take place in an acidic environment, for example, isomerization in case of pravastatin (Serrajuddin, A. T. M. et al, Biopharm. Sci. 80, 830-834, 1991; Kearney, A. S. et al, Pharm. Res. 10, 1993, 1461-1465).

Statins and related compounds are in the form of a cyclic ester—lactone, therefore, among others they are also sensitive to an alkaline medium, where they are transformed to an acid form.

Compounds in the environment which increase acidity or alkalinity of the environment trigger degradation reactions of an active substance sensitive to acidic or alkaline environment. Carbon dioxide in the presence of humidity or water, in which it is freely soluble, forms carbonic acid which increases the acidity of the environment.

Light and in particular UV light induces degradation reactions of active substances, especially organic ones. It is known that among others levofloxacin (Sato, Y. Y. E. and Moroi, R., Arzneim, Forsch./Drug Res. 43, 1993, 601-606) and atorvastatin are also sensitive to light (Hurley, T. R. et al, Tetrahedron 49, 1993, 1979-1984).

Oxygen induces oxidation, that is, oxidative degradation reactions of an active substance and/or pharmaceutical excipients resulting in formation of the reactive sites and/or degradation products which lead to further oxidation or further oxidative degradation reactions of the active substance and/or pharmaceutical excipients. For example, active substances known in the prior art to be sensitive to oxidation are:

Captopril, chlorpomazine, morphine, L-ascorbic acids vitamin E, phenylbutazone and tetracyclines (Waterman, K. C., et al, in "Stabilization of Pharmaceuticals to Oxidative Degradation", Pharmaceutical Development and Technology, 7(1), 2002, 1-32);

Omeprazole; and

HGM-CoA reductase inhibitors, e.g. pravastatin, atorvastatin, simvastatin and lovastatin (Javernik, S., et al, Pharmazie 56, 2001, 738-740; Smith, G. B., et al, Tetrahedron 49, 1993, 44474462; patent application P-200200244).

HMG-CoA reductase inhibitors (statins) are also among the active substances sensitive to pH of the environment, humidity, light, temperature, carbon dioxide and oxygen. They are known as the most effective therapeutically active substances for the treatment of dyslipidemias and cardiovascular disease, selected from the group consisting of dyslipidemia, hyperlipidemia, hypercholesterolemia, atherosclerosis, arteriosclerosis, coronary artery diseases, coronary heart disease and the like, associated with the metabolism of lipids and cholesterol. The mechanism of action of statins is the inhibition of the biosynthesis of cholesterol and other sterols in the liver of humans or animals. They are competitive inhibitors of HMG-CoA reductase or 3-hydroxy-3-methylglutaryl-coenzyme A reductase, an enzyme which catalyses the conversion of HMG-CoA to mevalonate in the liver of humans or animals, which is an important step in the biosynthesis of cholesterol in the liver. Recent studies indicate that, in addition to the said therapeutic effects, statins also have other therapeutic effects and thus they are useful for the treatment of diseases, abnormal conditions and disorders which are selected from the group consisting of vascular disorders, inflammatory disease, allergic disease, neurodegenerative disease, malignant disease, viral disease (WO 0158443), abnormal bone states, (WO 0137876), amyloid-β precursor protein processing disorders such as Alzheimer's disease or Down's Syndrome (WO 0132161).

Among the statins, for example, the following are known: pravastatin, atorvastatin simvastatin, lovastatin, mevastatin or compactin, fluvastatin or fluindostatin, cer(i)vastatin or rivastatin, rosuvastatin or visastatin, and itavastatin or pitavastatin, or nisvastatin.

Pravastatin is chemically (betaR*, deltaR,1S,2S,6S,8S, 8aR)-1,2,6,8,8a-hexahydro-beta, delta, 6-trihydroxy-2-methyl-8-((2S)-2-methyl-1-oxobutoxy)-1-naphthalene heptanoic acid. A sodium salt of said acid is sodium pravastatin. It was described first time in U.S. Pat. No. 4,346,227.

Atorvastatin is chemically a (R—(R*,R*))-2-(4-fluorophenyl-beta, delta-dihydroxy-5-(1-methylethyl)-3-phenyl-4-((phenylamino)carbonyl)-1H-pyrrole-1-heptanoic acid hemicalcium salt. It was described first time in U.S. Pat. No. 5,273,995.

Rosuvastatin is chemically (2:1) (3R,5S,6E)-7-(4-(4-fluorophenyl)-6-(1-methylethyl)-2-(methyl(methylsulfonyl) amino)-5-pyrimidinyl)-3,5-dihydroxy-6-heptenoic acid calcium salt. It was described first time in U.S. Pat. No. 5,260, 440.

Fluvastatin is chemically R*,S*-(E)-(+−)-7-(3-(4-fluorophenyl)-1-(1-methylethyl)-1H-indol-2-yl)-3,5-dihydroxy-6-heptenoic acid. Fluvastatin sodium is a sodium salt of said acid. It was described first time in European patent 114027.

Simvastatin is chemically (1S-(1alpha, 3alpha, 7beta, 8beta (2S*, 4S*) 8a beta))-1,2,3,7,8,8a-hexahydro-3,7-dimethyl-8-(2-(tetrahydro-4-hydroxy-6-oxo-2H-pyran-2-yl) ethyl)-1-naphthalenyl-2,2-dimethylbutanoate. It was described first time in U.S. Pat. No. 4,444,784.

Lovastatin is chemically (1S-(1alpha, 3alpha, 7beta, 8beta (2S*, 4S*) 8a beta))-1,2,3,7,8,8a-hexahydro-3,7-dimethyl-8-(2-(tetrahydro-4-hydroxy-6-oxo-2H-pyran-2-yl)ethyl)-1-naphthalenyl-2-methylbutanoate. It was described first time in U.S. Pat. No. 4,231,938 and JP 8425599.

Itavastatin is chemically (S—(R*,S*-(E)))-7-(2-cyclopropyl-4-(4-fluorophenyl)-3-quinolynyl)-3,5-dihydroxy-6-heptenoic acid. Pitavastatin is a lactone form of itavastatin. They were described first time in European patent no. 304063 and U.S. Pat. No. 5,011,930, respectively.

Mevastatin is chemically (3R,5R)-3,5-dihydroxy-7-((1S, 2S,6S,8S,8aR)-2-methyl-8-((2S)-2-methylbutanoyl)oxy)-1, 2,6,7,8,8a-hexahydronaphthalen-1-yl)heptanoic acid. It was described first time U.S. Pat. No. 3,983,140.

Cerivastatin is chemically (S—(R*,S*-(E)))-7-(4-(4-fluorophenyl)-5-(methoxymethyl)-2,6-bis(1-methylethyl)-3-pyridinyl)-3,5-dihydroxy-6-heptenoic acid. It was described first time in European patent no. 491226.

Many of the above statins are sensitive in particular to environmental influences, for example, atmospheric influences and pH of the environment. In the prior art it is known that certain statins are sensitive to acidic environment (low pH values) wherein they are degraded to their lactone forms and different isomers. For example, pravastatin, atorvastatin, itavastatin, and fluvastatin are converted to their lactone forms in an acidic environment.

In the prior art it is also known that statins which are in the lactone form, e.g. lovastatin and simvastatin, are sensitive to alkaline environment wherein they are converted to the acid form.

The sensitivity of different pharmaceutical active substances to oxidative degradation is described by Waterman, K. C., et al, in "Stabilization of Pharmaceuticals to Oxidative Degradation", Pharmaceutical Development and Technology, 7(1), 2002, 1-32, and possible approaches to stabilize pharmaceutical active substances against oxidative degradation are also presented. The above mentioned article suggests that study of oxidative mechanism in solid pharmaceutical dosage forms is difficult and demanding as indicated by few reports in said area. An active substance per se and more frequently an active substance in a pharmaceutical dosage form may oxidize. During the processing of drug to form a solid dosage form, it is possible to mechanically generate amorphous drug. The percent of formed amorphous form is usually small and below 1%. Amorphous drug regions have greater mobility and lack crystal-lattice stabilization energy, and as a result oxygen permeability and solubility will be higher. Greater mobility and higher oxygen concentration present in amorphous active substance also facilitate electron transfer to oxygen. (Waterman, K. C., et al, Stabilization of Pharmaceuticals to Oxidative Degradation, Pharmaceutical Development and Technology, 7(1), 2002, 1-32).

Byrn, S. R., et al. (Solid-State Chemistry of Drugs, $2^{nd}$ Ed., SSCI, West Lafayette, 1999) disclose that molecular oxygen from atmosphere reacts with organic crystals and said reactivity depends on a crystal form and morphology, respectively, which determines permeability to oxygen and its solubility in the crystal lattice. In some examples the reactivity decreases with increased melting point indicating that higher crystalline lattice energy inhibits diffusion of oxygen.

It is in general more difficult to remove an electron from a drug when it is more positively charged. Therefore drug stability against oxidation is often greater under lower pH conditions. The sensitivity of an active substance to oxidation also depends on a pharmaceutical dosage form per se and pharmaceutical excipients in it. Pharmaceutical excipients also influence oxidation of the active substance in a pharmaceutical dosage form. They can potentially solvate some of the active substances either directly or by bringing in low levels of moisture. In a solid solution form, the active substance will be amorphous with all the corresponding reactivity discussed above. Excipients themselves can be a source of oxidants or metals (e.g. present impurities) and may be involved in occurrence of mobile oxidative species, such as peroxyl radicals, superoxide and hydroxyl radicals. This depends on the hydrogen bond strength of the excipient and whether there are good electron donor sites (e.g. amines). Peroxide impurities are often present in polymeric excipients and they are a major source of oxidation in pharmaceutical formulations. (Waterman, K. C., et al, Stabilization of Pharmaceuticals to Oxidative Degradation, Pharmaceutical Development and Technology, 7(1), 2002, 1-32).

In the studies we have found that some of the above statins are particularly sensitive to oxidation. Among them particularly sensitive are certain polymorphic or amorphous forms of atorvastatin, pravastatin, lovastatin, simvastatin and rosuvastatin.

The influence of oxygen on occurrence of degradation products of amorphous and four polymorphic forms of atorvastatin was investigated. The samples of amorphous atorvastatin and polymorphic forms I to IV of atorvastatin were exposed at 80° C. in normal (air) and oxygen atmosphere for 3 days. The assay of oxidation products was determined by liquid chromatography. All of the chosen forms of atorvastatin stored at 4° C. were analyzed as the reference samples.

TABLE 1

Increase of the degradation products of amorphous and different crystalline forms of atorvastatin stored at 80° C. in normal (air) and oxygen atmosphere for 3 days in respect to reference samples

| Increase of degradation products % | Amorphous ATV | Crystalline form I | Crystalline form II | Crystalline form III | Crystalline form IV |
|---|---|---|---|---|---|
| AIR | 1.04 | 0.04 | 0.25 | 0.11 | 1.14 |
| OXYGEN | 3.4 | 0.07 | 0.71 | 0.47 | 3.67 |

The above study shows that different forms of atorvastatin are variably sensitive to the impact of oxygen regarding the formation of degradation products. In case of amorphous atorvastatin and crystalline form IV the percent of oxidation degradation products essentially increased in oxygen atmosphere and normal atmosphere (air). In case of crystalline forms I, II and III the percent of oxidation degradation products was low in air atmosphere, while in oxygen atmosphere the percent of oxidation degradation products increased in crystalline forms II and III.

We can conclude that crystalline form I is stable to oxygen and oxidation, crystalline forms II and III are slightly sensitive to oxidation and crystalline form IV and amorphous atorvastatin are highly sensitive to oxidation.

PRIOR ART

The patent documents which solve the problem of maintaining the stability of some of the listed statins at low pH environment are:

for atorvastatin with alkaline compounds U.S. Pat. No. 5,686,104, U.S. Pat. No. 6,126,971, WO 9416693 and European patent no. 680320, and with alkaline and/or buffering compounds WO 02072073;

for pravastatin with alkaline compounds European patent no. 336298, U.S. Pat. No. 5,030,447 and U.S. Pat. No. 5,180,589, with alkaline and/or buffering compounds and other excipients WO 02076376, with buffering compounds WO 03000239 and WO 03000177;

for fluvastatin with alkaline medium European patent no. 547000 and U.S. Pat. No. 5,356,896;

for itavastatin with alkaline compound WO 9723200 European patent no. 814782;

for atorvastatin, pravastatin and other statins with polymers which contain amino groups or amido groups, WO 0176566 and U.S. Pat. No. 20020035142;

for atorvastatin, pravastatin, fluvastatin, cerivastatin, mevastatin, pitavastatin, rosuvastatin, lovastatin and simvastatin with amino sugars WO 02089788;

for atorvastatin, pravastatin, fluvastatin and cerivastatin with buffering compounds WO 0035425;

for atorvastatin, pravastatin, fluvastatin and cerivastatin with alkaline and/or buffering compound WO 0193860.

Among the patent documents which solve the problem of maintaining the stability of some of the listed statins at high humidity and temperature is WO 9949896 which discloses stabilization of pravastatin with beta-cyclodextrin.

A review of the known methods (antioxidants, packaging) for stabilization of the active substance from oxidation is presented, e.g., in Waterman, K. C., et al, Pharm. Dev. and Technol. 7, 2002, 1-32.

For the prevention or reduction of active substances oxidation in a pharmaceutical dosage form, different approaches are used for example:

increase of the concentration of the active substance in a pharmaceutical dosage form when oxidation is caused by peroxide and metallic impurities in pharmaceutical excipients;

addition of chelating agents (such as, e.g. citric acid, EDTA, fumaric and malic acid) to the formulation for mitigation of metallic impurities;

use of high-purity pharmaceutical excipients;

use of alternative excipients or decrease their amount in the pharmaceutical dosage form, especially when peroxide impurities are the cause of oxidation;

use of antioxidants which can reduce formation of peroxides, but maybe less effective at eliminating peroxides already present in a dosage form.

For individual active substances there is no general way to predict optimal solution for oxidation prevention and the publications available are scarce (Waterman, K. C., et al, Stabilization of Pharmaceuticals to Oxidative Degradation, Pharmaceutical Development and Technology, 7(1), 2002, 1-32).

Among suitable antioxidants there are described:
chain terminators (e.g. thiols and phenols);
sacrificial reductants which are oxidized more readily than the active substance and thus remove present oxygen (e.g. sulfites and ascorbic acid) wherein their combination may act synergistically (e.g. a combination of ascorbic palmitate and tocopherol);
peroxide quenchers (e.g. $Fe^{2+}$) which degrade peroxides by Fentonprocess. Their use is limited because in this process a free hydroxyl radical is formed.
cyclodextrins which cover the site of an active substance, subjected to oxidation (Waterman, K. C., et al, Stabilization of Pharmaceuticals to Oxidative Degradation, Pharmaceutical Development and Technology, 7(1), 2002, 1-32).

In addition to above-mentioned solutions, prevention from oxidation can be achieved by packaging where the oxygen content in a space surrounding an active substance and permeability of oxygen through the package walls and cap are regulated. It is possible to reduce the oxygen content contained in the package by packaging under nitrogen atmosphere. When drugs are concerned, a blister is the most suitable form of packaging under controlled atmosphere. Blisters which are less permeable or impermeable to oxygen (e.g. foil-foil) are usually more expensive. Despite the numerous different described methods of stabilization in different ways, for example, with the addition of antioxidants to a pharmaceutical dosage forms by packaging a pharmaceutical formulation into a suitable package, these solutions have not shown to be convenient for all active substances and all markets, respectively (Waterman, K. C., et al, Stabilization of Pharmaceuticals to Oxidative Degradation, Pharmaceutical Development and Technology, 7(1), 2002, 1-32).

Different types of packaging materials for the protection of pharmaceutical active substances and pharmaceutical formulation from oxidation are disclosed in numerous patents.

WO 0076879 discloses the barrier pack comprising a cover portion bonded to a base portion to form a sealed unit package wherein the cover portion comprises at least one cavity containing a product, and the cover portion and/or base portion has an absorbing agent material (desiccant).

European patent no. 370755 discloses a packaging material for drugs which is specially designed with the foil comprising an inner polypropylene film, an intermediate olefin film and an outer polypropylene film. Further said package may also comprise aluminium foil.

European patent no. 595800 discloses a packaging material comprising a layer which removes oxygen from a package by means of an enzyme reaction; the package has an outer film which is impermeable to gas and water vapours (e.g. a laminate such as polyamide and polyethylene), an inner film which is permeable to gas and impermeable to liquid (e.g. polyethylene and copolymers thereof), and intermediate film which removes oxygen and comprises a liquid phase with an enzyme for oxygen removal (oxidase such as glucose oxidase) wherein an insoluble filler is suspended in a liquid phase.

The methods of coating the substances or products sensitive to oxidation with coatings which protect said substances or products from oxidation are known in the prior art in the food industry. The coatings from milk proteins are described which also comprise carboxymethylcellulose to prevent oxidative browning of apples and potatoes (Le Tien, C., et al, Protein Coatings Prevent Oxidative Browning of Apples and Potatoes, Journal of Food Science Vol. 66, No. 4, 2001, 512-516).

In the field of pharmacy the use of ethylcellulose for coating of ascorbic acid granules for protection against oxidation is known (Wade, A., et al, Handbook of Pharmaceutical Excipients, 2nd Ed, American Pharmaceutical Association, Washington, and The Pharmaceutical Press, London, 1994, 186-190).

Sensitivity of lovastatin to oxidation and its stabilisation and protection from oxidation with natural antioxidants are described by Javernik, S., et al, in Pharmazie 56(9), September 2001, 738-740.

Sensitivities of lovastatin and simvastatin and other substances (e.g. alkaline substances with pKa from 1 to 10 and from 5 to 9, respectively, which further have redox potential of about 1300 mV and about 1000 mV, respectively) to oxidation are disclosed in U.S. Pat. No. 20020132359 and European patent no. 1241110 which solve the problem of oxidation by a special package form where each unit dose comprising oxygen-sensitive drug, is individually encapsulated in the pharmaceutical packaging construction such that when one unit dose is dispensed the other unit doses remained encapsulated. An oxygen-absorber is also incorporated into the construction. Oxygen absorber is selected from the group consisting of absorbents which are activated themselves or by moisture (e.g. copper powder, zinc powder), UV rays, electron ray, irradiation, microwaves or a combination thereof.

Prevention of oxidation of atorvastatin by means of suitable packaging (in the nitrogen atmosphere) is also disclosed in the patent application P-200200244.

In the patent documents and other prior art documents no documents have been found relating to different modes of solving the problem of protection of pharmaceutical active substances and pharmaceutical dosage form from oxidation.

Therefore, the object of the present invention is to protect and consequently stabilize the active substance, sensitive to environmental influences, and to stabilize the pharmaceutical dosage form comprising said active substance and one or more pharmaceutical excipients. Further, the object of the present invention is to protect and consequently stabilize the active substance which is sensitive to oxidation and environmental humidity, and to stabilize the pharmaceutical dosage form comprising said active substance and one or more pharmaceutical excipients. Preferably, the object of the present invention is to protect and consequently stabilize the active substance, which is statin, to environmental influences and preferably to oxidation by preventing the contact between the active substance and oxygen thus preventing occurrence of degradation products of the active substance and preferably oxidative degradation products as well as degradation products of the pharmaceutical excipients.

DESCRIPTION OF THE INVENTION

The first object of the present invention is a coating which affords protection and consequently stability of an active substance and one or more pharmaceutical excipients and/or pharmaceutical dosage form from environmental influences and in particular from oxidation and/or environmental humidity.

In the context of the present invention the term coating of the present invention means a layer of material applied directly onto the core which is either an active substance itself or an active substance with one or more pharmaceutical excipients in the form of particles of regular or irregular shapes such as microcapsules, microspheres, granules, pellets and the like, or a pharmaceutical dosage form selected from the group consisting of tablets, capsules or similar forms known in the prior art. Said coating affords protection of the active substance and one or more pharmaceutical excipients, respectively, from environmental influences and in particular from oxidation and/or environmental humidity. Additionally, the coating of the present invention enables release of the active substance in all parts of gastrointestinal tract, regardless of environmental pH value.

The active substance of the present invention is an active substance which is sensitive to environmental influences and is selected from the group consisting of HMG-CoA reductase inhibitor, captopril, chlorpromazine, morphine, L-ascorbic acid, vitamin E, phenylbutazone, tetracyclines and omeprazole. Preferably an active substance of the present invention, sensitive to oxidation and environmental humidity is a HMG-CoA reductase inhibitor selected from the group consisting of pravastatin, atorvastatin, rosuvastatin, itavastatin, simvastatin and lovastatin.

In the context of the present invention the coating is a layer of material comprising one or more film-formers. A suitable film-former is any film-former which applied in the form of a coating onto the particle or the core of the pharmaceutical dosage form comprising the active substance which is sensitive to environment influences, affords protection of the active substance from environmental influences and preferably against oxidation and/or environmental humidity. Most preferably such film-former is any film-former which affords protection of the active substance from oxidation. Said film-former is selected from the group consisting of polyvinyl alcohol (PVA) and derivatives of cellulose. Among the derivatives of cellulose a film-former is preferably sodium carboxymethylcellulose (NaCMC) or hydroxyethyl cellulose (HEC) and most preferably sodium carboxymethylcellulose (NaCMC). A film-former may be also a combination of one or more said film-formers in all possible ratios. A film former is added in concentrations 40-100%, preferably in concentrations 60-95%, more preferably in concentrations 70-90% to the amount of solids in a coating.

Among film-forming polymers with desired properties sodium carboxymethylcellulose (NaCMC) exhibits especially low permeability to oxygen if the thickness of NaCMC coating is sufficient. On the other hand, NaCMC coating swells in contact with liquid water and forms an insoluble gel-like film with extremely low permeability to water. This could prevent the tablet disintegration and the release of the active substance. In addition, NaCMC gel becomes very viscous and the polymer chains cross-link through lactonization between carboxylic acid and free hydroxyl groups in the acidic gastric environment. Both of these mechanisms could prevent the permeation of water through the coating to the tablet core and therefore prevent release of the active substance.

It was surprisingly found that with addition of suitable excipients, selected from the group consisting of buffering agents, alkalizing agents and surface active agents the above weaknesses of NaCMC coating are overcome.

The buffering component of the coating of the present invention is a salt of weak acid and strong base or a salt of strong acid and weak base or other similar substance which maintains the pH within the determined range. The buffering component may be selected from the group consisting of:
a) alkali metal salts, alkali-earth metal salts and ammonium salts of citric acid, ascorbic acid, maleic acid, sorbic acid, succinic acid, benzoic acid, phosphoric acid, carbonic acid, sulfuric acid, nitric acid, boric acid and silicic acid;
b) amines in combination with a strong or weak acid, such as trometamine (TRIS), EDTA;
c) ion exchangers; and
d) any combinations thereof.

Buffering components are added in concentrations 0-20%, preferably in concentrations 0-10% to the amount of solids in the coating.

The alkalizing component of the coating of the present invention is selected from the group consisting of organic or inorganic compounds which contain the groups having alkaline action and may be selected from the group consisting of:
a) oxides and hydroxides of alkaline and/or alkali-earth metals, oxides of the 4, 5 and/or 6 group of the periodic system such as MgO, MgOH, NaOH, $Ca(OH)_2$;
b) amines, such as trometamine (TRIS)), ethanolamine, diethanolamine, triethanolamine, N-methyl-glucamine, glucosamine, ethylenediamine, diethylamine, triethylamine, isopropylamine, diisopropylamine;
c) alkali amino acids, such as arginine, histidine and lysine.

Alkalizing components are added in concentrations 0-20%, preferably In concentrations 0-10% to the amount of solids in the coating.

The surfactant of the coating of the present invention may be selected from the group consisting of ionic surfactants such as sodium lauryl sulfate, nonionic surfactants such as different types of poloxamers such as polyoxyethylene and polyoxypropylene copolymers, natural and synthetic lecithins and esters of sorbitan and fatty acids such as Span® (Atlas Chemie), polyoxyethylenesorbitan and fatty acid esters such as polyoxyethylene sorbitan monooleate such as Polysorbate 80 or Tween® (Atlas Chemie), polyoxyethylated hydrogenated castor oil such as Cremophor® (BASF), polyoxyethylene stearates such as Myrj® (Atlas Chemie) or cationic surfactants such as cetylpyridine chloride or any of combinations of said surfactants. Surfactants are added in concentrations 0-20%, preferably in concentrations 0-10%, more preferably in concentrations 0-5% to the amount of solids in the coating.

In the context of the present invention the coating may further comprise one or more pharmaceutically acceptable pharmaceutical excipients which are selected from the group consisting of one or more plasticizers, one or more viscosity-increasing agents of a coating dispersion, one or more fillers, one or more lubricants or glidants, one or more colorants, and additional pharmaceutical excipients which are used in the prior art for coatings.

The plasticizer of the coating of the present invention may be selected from the group consisting of glycerol, diglycerol, ethanolamines, ethylene glycol, polyethylene glycols, glycerol α-monomethyl ether, glycerol monochloridine, 2,3-butylene glycol, 1,2,6-hexanetriol, 2-nitro-2-methyl-1,3-propandiol, propylene glycol, glyceryl triaccetate, polyoxyethylenelpolyoxypropylene copolymers, triethyl citrate, oleic acid, fractionated coconut oil and any combinations thereof. The plasticizer is added in concentrations 1-50%, preferably in concentrations 5-40%, more preferably in concentrations 10-30% to the amount of the film-former in the coating.

The viscosity-increasing agent of the coating dispersion of the present invention may be selected from the group consisting of carboxymethylcellulose, hydroxypropyl methylcellulose, hydroxypropyl cellulose, xanthan, alginates, chitosan and any combinations thereof. The viscosity-increasing agents are added in concentrations 0-50%, preferably in concentrations 0-20% to the amount of solids in the coating.

The filler of the coating of the present invention may be selected from the group consisting of lactose, polydextrose, maltodextrin, mannitol, starch and any combinations thereof. Fillers are added in concentrations 0-15%, preferably in concentrations 0-5% to the amount of solids in the coating.

The lubricant or glidant of the coating of the present invention may be selected from the group consisting of talc, magnesium stearate, colloidal silicon dioxide, stearic acid, calcium stearate and any combinations thereof. The lubricants or glidants are added in concentrations 0-40%, preferably in concentrations 0-25% to the amount of solids in the coating.

The colorant of the coating of the present invention may be selected from the group consisting of aluminium lakes, insoluble pigments, water-soluble dyes, titanium di-oxide, talc, and any combinations thereof. The colorants are added in concentrations 0-20%, preferably in concentrations 0-10% to the amount of solids in the coating.

Other pharmaceutical excipients of the coating of the present invention are the substances used in this field of art for coatings and are known in the prior art.

A solvent of the coating dispersion may be water, different combinations of organic solvents or combinations of organic solvents and water.

The thickness of the coating of the present invention applied directly onto the core which is either an active substance itself or an active substance with one or more excipients in the form of particles of regular or irregular shapes such as microcapsules, microspheres, granules, pellets and the like, or a pharmaceutical dosage form selected from the group consisting of tablets, capsules or similar forms known in the prior art should be sufficient to achieve its functionality, this means impermeability to oxygen and/or water. The thickness of the coating is in the range 5-200 µm, preferably 5-100 µm.

The amount of the coating applied can be estimated from the following equation:

$$w = \frac{dS_{core}\rho_c}{m_{core}}$$

w weight of coating in respect to core mass
d thickness of coating
$S_{core}$ surface area of the core
$\rho_c$ density of the coating
$m_{core}$ mass of the core Further object of the present invention are the coated particles which are particles of the active substance or the particles of the active substance and one or more pharmaceutical excipients in the form of particles of regular or irregular shapes, such as microcapsules, microspheres, granules, pellets and the like said particles are protected from environmental influences and in particular from oxidation and/or environmental humidity by coating. Said particles are embedded either in an uncoated pharmaceutical dosage form or in a coated pharmaceutical dosage form wherein the coating of the present invention affords protection and consequently stability of the active substance and one or more pharmaceutical excipients from environmental influences and in particular from oxidation and/or environmental humidity. When coated particles are embedded in a coated pharmaceutical dosage form said coating could be also any other in the prior art known coating.

The coated particles of the present invention comprise (a) an active substance or an active substance and one or more pharmaceutical excipients wherein the active substance is sensitive to environmental influences and (b) the coating of the present invention which affords protection of the active substance and one or more pharmaceutical excipients from environmental influences.

The coated particles of the present invention comprise (a) an active substance or an active substance and one or more pharmaceutical excipients wherein the active substance is sensitive to oxidation and environmental humidity and (b) the coating of the present invention which affords protection of the active substance and pharmaceutical excipients from oxidation and/or environmental humidity.

The coated particles of the present invention comprise (a) an active substance or an active substance and one or more pharmaceutical excipients wherein the active substance is sensitive to oxidation and (b) the coating of the present invention which affords protection of the active substance and pharmaceutical excipients from oxidation.

The active substance of the present invention embedded in the coated particles of the present invention is selected from the group consisting of HMG-CoA reductase inhibitor, captopril, chlorpromazine, morphine, L-ascorbic acid, vitamin E, phenylbutazone tetracyclines and omeprazole. Preferably an active substance of the present invention, is an HMG-CoA reductase inhibitor selected from the group consisting of pravastatin, atorvastatin, rosuvastatin, itavastatin, simvastatin and lovastatin.

The pharmaceutical dosage forms of the present invention are the coated or uncoated pharmaceutical dosage forms.

Further object of the present invention is the coated pharmaceutical dosage form which comprises:
a) a mixture of one or more coated particles of the present invention and/or one or more uncoated particles containing one or more active substances of the present invention which are sensitive to environmental influences, preferably to oxidation and environmental humidity and most preferably to oxidation;
b) one or more pharmaceutical excipients;
c) and
the coating of the present invention which provides protection of one or more active substances and one or more pharmaceutical excipients and the pharmaceutical dosage form from environmental influences, preferably from oxidation and/or environmental humidity and most preferably from oxidation or
any other coating known in the prior art when the coated particles of the present invention are embedded in the coated pharmaceutical dosage form.

The uncoated particles in the context of the present invention are the particles which do not include the coating of the present invention or any other coating known in the prior art.

Further object of the present invention is the uncoated pharmaceutical dosage form which comprises:
a) one or more coated particles of the present invention containing one or more active substances of the present invention which are sensitive to environmental influences, preferably to oxidation and environmental humidity and most preferably to oxidation;
b) one or more pharmaceutical excipients.

The active substance of the present invention embedded in the coated or uncoated pharmaceutical dosage form of the present invention is selected from the group consisting of HMG-CoA reductase inhibitor, captopril, chlorpromazine, morphine, L-ascorbic acid, vitamin E, phenylbutazone, tetracyclines and omeprazole. Preferably an active substance of the present invention is an HMG-CoA reductase inhibitor selected from the group consisting of pravastatin, atorvastatin, rosuvastatin, itavastatin, simvastatin and lovastatin.

The pharmaceutical dosage form of the present invention and particles of regular or irregular shapes of the present invention such as microcapsules, microspheres, granules, pellets and the like comprise one or more pharmaceutical excipients which are selected from the group consisting of:
a) one or more fillers;
b) one or more binders;
c) one or more disintegrants;
d) one or more lubricants or glidants;
e) one or more buffering components;
f) one or more alkalizing components;
g) one or more surfactants;
h) and other components for solid pharmaceutical dosage form known in the prior art and which are selected from the group consisting of colorants, flavors and adsorbing substances.

The filler of the pharmaceutical dosage form of the present invention may be selected from the group consisting of microcrystalline cellulose (MCC), modified forms of microcrystalline cellulose, lactose, sugars, different types of starch, modified forms of starch, mannitol, sorbitol and other polyoles, dextrin, dextran and maltodextrin, calcium carbonate, calcium phosphate and/or hydrogen phosphate, sulfate and any combinations thereof. Fillers are added in concentrations 1-99% to the total weight of the pharmaceutical dosage form.

The binder of the pharmaceutical dosage form of the present invention may be selected from the group consisting of lactose, different types of starch, modified forms of starch, dextrin, dextran and maltodextrin, microcrystalline cellulose (MCC), sugars, polyethylene glycols, hydroxypropyl cellulose, hydroxypropyl methylcellulose, ethylcellulose, hydroxyethyl cellulose, methylcellulose, carboxymethylcellulose, sodium carboxymethylcellulose, gelatin, acacia, tragacanth, polyvinylpyrrolidone, magnesium aluminium silicate and any combinations thereof. Binders are added in concentrations 0.5-20% to the total mass of the pharmaceutical dosage form.

The disintegrant of the pharmaceutical dosage form of the present invention may be selected from the group consisting of crosslinked sodium carboxymethylcellulose, crosslinked polyvinylpyrrolidone, crosslinked carboxymethyl starch, different types of starch and microcrystalline cellulose, magnesium aluminium silicate, polacrilin potassium and any combinations thereof. Disintegrants are added in concentrations 2-20% to the total mass of the pharmaceutical dosage form.

The lubricant of the pharmaceutical dosage form of the present invention may be selected from the group consisting of magnesium, calcium and zinc stearate, calcium behenate, sodium stearyl fumarate, talc, magnesium trisilicate, stearic acid, palmitic acid, carnauba wax, silicon dioxide and any combinations thereof. Lubricants or glidants are added in concentrations 0.1-10% to the total mass of the pharmaceutical dosage form.

The buffering component of the pharmaceutical dosage form of the present invention is a salt of weak acid and strong base or a salt of strong acid and weak base or other similar substance which maintains the pH within the determined range. The buffering component may be selected from the group consisting of:
a) alkali metal salts, alkali-earth-metal salts and ammonium salts of citric acid, ascorbic acid, malic acid, sorbic acid, succinic acid, benzoic acid, phosphoric acid, carbonic acid, sulfuric acid, nitric acid, boric acid and silicic acid;
b) amines in a combination with a strong or weak acid, such as trometamine (TRIS), EDTA;
c) ion exchangers; and
d) any combinations thereof.

Buffering components are added in concentrations 0-50% to the total mass of the pharmaceutical dosage form.

The alkalizing component of the pharmaceutical dosage form of the present invention is selected from the group consisting of organic or inorganic compounds which contain the groups having alkaline action and may be selected from the group consisting of:
a) oxides and hydroxides of alkaline and/or alkali-earth metals, oxides of the 4, 5 and/or 6 group of the periodic system such as MgO, MgOH, NaOH, $Ca(OH)_2$;
b) amines such as trometamine (TRIS), ethanolamine, diethanolamine, triethanolamine, N-methyl-glucamine, glucosamine, ethylenediamine, diethylamine, triethylamine, isopropylamine, diisopropylamine;
c) alkali amino acids such as, e.g. arginine, histidine and lysine.

Alkalizing components are added in concentrations 0-50% to the total mass of the pharmaceutical dosage form.

The surfactant of the pharmaceutical dosage form of the present invention may be selected from the group consisting of ionic surfactants such as sodium lauryl sulfate, nonionic surfactants such as different types of poloxamers (copolymers of polyoxyethylene and polyoxypropylene), natural or synthesized lecithins and esters of sorbitan and fatty acids (such as Span® (Atlas Chemie)), esters of polyoxyethylene-sorbitan and fatty acids (e.g. polyoxyethylene (20) sorbitan monooleate such as Polysorbate 80 and Tween® ((Atlas Chemie), respectively), polyoxyethylated hydrogenated castor oil (such as Cremophor® (BASF)), polyoxyethylene stearates (such as Myrj® (Atlas Chemie)) or cationic surfactants such as cetylpyridine chloride or any combination of said surfactants. Surfactants are added in concentrations 0-15% to the total mass of the pharmaceutical dosage form.

Other components for solid pharmaceutical dosage form are the components which are known from the prior art and are conventional and used in the art of solid pharmaceutical dosage form. They are selected from the group consisting of colorants, flavoring agents and adsorbing materials.

The pharmaceutical dosage form of the present invention is preferably the solid pharmaceutical dosage form.

The pharmaceutical dosage form of the present invention comprises active substances sensitive to environmental humidity have water content bellow 5%, preferably below 4% and the most preferably below 3% by weight of the entire pharmaceutical dosage form. The pharmaceutical dosage form of the present invention prevents conversion of the active substance HMG-CoA reductase inhibitor from a hydroxyl acid form to a lactone form under the conditions of low humidity, that is, at 5% loss on drying (LOD bellow 5%), preferably LOD bellow 4% and most preferably bellow 3%.

The object of the present invention is also the process for the preparation of the coated particles of the present invention and the pharmaceutical dosage forms of the present invention.

Particles of regular or irregular shapes such as microcapsules, microspheres, granules, pellets and the like, and pharmaceutical dosage forms such as tablets, capsules and the like, of the present invention can be prepared with any in prior art known process, for example:

A mixture of one or more coated and/or one or more uncoated active substances, a filler, a binder, a buffering agent, an alkalizing agent, a disintegrant and if required a surfactant and other conventional ingredients for a solid pharmaceutical dosage form are homogenized in suitable mixers, the mixture is compacted in suitable compaction machines or slugged in slugging machines or conventional tablet presses, the compacts and or slugs are triturated and/or sieved, fillers, buffering agents, disintegrants, glidants, lubricants and other conventional pharmaceutical excipients for tablets or capsules are added, and the mixture is homogenized. The resulting mixture is compressed into tablets or filled into capsules;

A mixture of one or more coated and/or one or more uncoated therapeutic active substances, a filler, a binder, buffering agent, alkalizing agent, a disintegrant and if required a surfactant and other conventional ingredients for a solid pharmaceutical dosage form is homogenized in suitable mixers, glidants and lubricants are added and the mixture is homogenized. The resulting mixture is compressed into tablets or filled into capsules;

A solution of a buffering component and if required a binder, a surfactant and a disintegrant is sprayed in the warm air flow onto a filler, a mixture of one or more coated and/or uncoated therapeutic active substances is added, and if required a binder, a buffering component, alkalizing agent, a disintegrant, a surfactant and other conventional components for solid pharmaceutical dosage forms, the mixture is homogeneously mixed in suitable mixers, glidants and lubricants are added and the mixture is homogenized. The resulting mixture is compressed into tablets or filled into capsules;

A mixture of one or more coated and/or one or more uncoated therapeutic active substance, a filler, a binder, a buffering agent, alkalizing agent, a disintegrant and if required a surfactant and other conventional ingredients for a solid pharmaceutical dosage forms is homogenized in suitable mixers, granulated with a suitable solvent such as water, ethanol, methanol, isopropyl alcohol, n-butyl alcohol, acetone, diethylether, ethylacetate, isopropylacetate, methylacetate, dichloromethane, chloroform, mixtures of said solvents such as ethanol and acetone, methanol and acetone, dichloromethane and methanol, and mixtures thereof. The resulting granulate is dried in suitable dryers such as standard plate dryers, fluidized bed dryers, vacuum and microwave dryers, at a temperature not exceeding 60° C. To the dried granulate are added fillers, disintegrants, buffering agents, alkalizing agent, glidants and lubricants and if required other conventional ingredients for solid pharmaceutical dosage forms. The resulting mixture is homogenized and compressed into tablets or filled into capsules.

When required, the active substance, particles of regular or irregular shapes, such as microcapsules, microspheres, granules, pellets and the like, and pharmaceutical dosage forms such as tablets, capsules and the like, may be coated with the coating of the present invention and which provides protection of the active substance from environmental factors, preferably from oxidation. In the case of said coated particles incorporated in pharmaceutical dosage forms such as tablets, capsules, and the like, said pharmaceutical dosage forms may be coated with any other in the prior art known coating.

Particles or pharmaceutical dosage forms of the present invention can be coated by any process known in the prior art, for example:

A mixture of one or more film formers, a plasticizer and optionally one or more excipients from following groups: viscosity-increasing agent, filler, glidant, colorant, surfactant, buffering component, alkalizing component and other excipients, is prepared by dispersing and dissolving in a solvent and then sprayed onto the active substance, particles of regular or irregular shapes such as, e.g. microcapsules, microspheres, granules, pellets and the like, and pharmaceutical dosage forms such as, e.g. tablets, capsules in suitable coating equipment.

If necessary, coating process can also be provided in an inert atmosphere, such as nitrogen, argon or carbon dioxide atmosphere.

The object of the present invention is further use of the active substance in the context of said invention for the preparation of the coated particles and/or pharmaceutical dosage forms for the treatment and the method of treatment of different diseases by administering the coated particles and/or pharmaceutical dosage forms wherein the diseases are selected from the group consisting of dyslipidemia, hyperlipidemia, hypercholesterolemia, atherosclerosis, arteriosclerosis, cardiovascular disease, coronary artery disease, coronary heart disease, vascular disorder, inflammatory disease, allergic disease, neurodegenerative disease, malignant disease, viral disease (WO 0158443), abnormal bone states (WO 0137876), amyloid-(precursor protein processing disorders such as Alzheimer's disease of Down's Syndrome (WO0132161).

The invention will be explained with reference to the accompanying examples, which are illustrative and should not be construed as limiting scope of the invention.

EXAMPLES

All herein presented examples referring to atorvastatin include amorphous atorvastatin Ca.

Example 1

Composition of One Coated Tablet 1.1. Tablet Core

TABLE 2

| Composition of the core | |
| --- | --- |
| Ingredient | Mass (mg) |
| Atorvastatin (in the form of atorvastatin Ca) | 20.00 |
| Microcrystalline cellulose | 143.20 |
| Lactose monohydrate | 34.80 |
| Crosslinked carboxymethylcellulose | 19.20 |

TABLE 2-continued

| Composition of the core | |
| --- | --- |
| Ingredient | Mass (mg) |
| Hydroxypropyl cellulose | 2.00 |
| Polysorbate 80 | 2.60 |
| Magnesium oxide | 26.00 |
| Colloidal silicon dioxide | 1.20 |
| Magnesium stearate | 1.00 |

Preparation of Tablet Core

Atorvastatin, half of microcrystalline cellulose, lactose monohydrate, half of crosslinked carboxymethylcellulose and 11% of the total magnesium oxide were homogeneously mixed and granulated with a solution of hydroxypropyl cellulose and polysorbate in water. The granulate was dried in a fluid bed dryer and the sieved granulate was homogeneously mixed with the other half of microcrystalline cellulose and crosslinked carboxymethylcellulose, the rest of magnesium oxide, colloidal silicon dioxide and magnesium stearate. The homogeneous granulate was compressed into tablets, mass 250 mg, on a conventional tablet press.

1.2. Tablet Coating

TABLE 3

| Composition of a coating | | |
| --- | --- | --- |
| | Weight of coating in respect to core mass (%) and mass of ingredients in a coating (mg) | |
| Coating ingredients | 6% | 8% |
| Sodium carboxymenthylcellulose | 14.00 mg | 18.64 mg |
| Glycerol | 1.40 mg | 1.86 mg |

Preparation of a Coating Dispersion and Coating of Tablet Cores

Sodium carboxymethylcellulose (Blanose CMC 7LF PH, Aqualon), (111.84 g) with viscosity 25 to 50 mPas and glycerol (11.16 g) while mixing were dissolved in water (2576.40 g). The resulting dispersion was sprayed onto the cores to obtain different coatings 6% and 8% by weight in respect to core mass. During the coating process the tablet mass was controlled and thus the mass of coating was determined.

1.3. Analysis of Stability of the Active Substance in the Pharmaceutical Dosage Form of Example 1 in Different Atmospheres The effect of the protective coating was tested by the stress test at 60° C. 14 days in nitrogen, air and oxygen atmosphere. The assay of oxidative products of atorvastatin in the tablets was determined by liquid chromatography. As reference sample the tablets stored at 4° C. were analyzed. Coated tablets were compared with uncoated tablet cores.

TABLE 4

Increase of the assay of degradation products of atorvastatin in the tablets stored 14 days at 60° C. in nitrogen, air and oxygen atmosphere versus the tablets stored at 4° C.

| Pharmaceutical dosage form | Weight of coating in respect to core mass (%) | Weight of glycerol in respect to mass of Na CMC (%) | Increase of the assay of degradation products in % in different atmospheres | | |
|---|---|---|---|---|---|
| | | | Nitrogen | Air | Oxygen |
| Reference of Example 1 - uncoated tablet | 0 | 0 | 0.24 | 1.01 | 3.45 |
| Coated tablet of Example 1 | 6 | 10 | 0.19 | 0.28 | 0.32 |
| Coated tablet of Example 1 | 8 | 10 | 0.38 | 0.32 | 0.19 |

An increase of the degradation products of atorvastatin in the uncoated tablet in comparison to the coated tablet of Example 1 is approximately three times greater for the samples in air atmosphere and more than ten times greater for the samples in oxygen atmosphere. The coating of Example 1 prevents ingress of oxygen to the tablet core and to the active substance thus preventing occurrence of degradation products of the active substance.

Example 2

Composition of One Coated Tablet 2.1. Tablet Core

TABLE 5

Composition of the core

| Ingredient | Mass (mg) |
|---|---|
| Atorvastatin (in the form of atorvastatin Ca) | 10.00 |
| Microcrystalline cellulose | 153.20 |
| Lactose monohydrate | 34.80 |
| Crosslinked carboxymethylcellulose | 19.20 |
| Hydroxypropyl cellulose | 2.00 |
| Polysorbate 80 | 2.60 |
| Magnesium oxide | 26.00 |
| Colloidal silicon dioxide | 1.20 |
| Magnesium stearate | 1.00 |

Preparation of Tablet Core

Atorvastatin, 53% of the total microcrystalline cellulose, lactose monohydrate, half of crosslinked carboxymethylcellulose and 11% of the total magnesium oxide were homogeneously mixed and granulated with a solution of hydroxypropyl cellulose and polysorbate in water. The granulate was dried in a fluid bed dryer and the sieved granulate was homogeneously mixed with the rest of microcrystalline cellulose, crosslinked carboxymethylcellulose and magnesium oxide, colloidal silicon dioxide and magnesium stearate. The homogeneous granulate was compressed into tablets, mass 250 mg, on a conventional tablet press.

2.2. Tablet Coating

TABLE 6

Composition of a coating

| Coating ingredients | Weight of coating in respect to core mass (%) and mass of ingredients in a coating (mg) | |
|---|---|---|
| | 6% | 8% |
| Sodium carboxymenthylcellulose | 14.000 mg | 18.640 mg |
| Glycerol | 1.400 mg | 1.860 mg |
| Titanium dioxide | 1.586 mg | 2.082 mg |
| Pigment yellow | 0.014 mg | 0.018 mg |

Preparation of a Coating Dispersion and Coating of Tablet Cores

Sodium carboxymethylcellulose (Blanose CMC 7LF PH, Aqualon), (111.84 g) with viscosity 25 to 50 mPas and glycerol (11.16 g) while mixing were dissolved in water (2576.40 g) and then while mixing a dispersion of coloring concentrate was added. A coloring concentrate was prepared by dispersing an aqueous dispersion of titanium dioxide (12.492 g) and pigment yellow (Sicopharm 10, BASF), (0.108 g). The resulting dispersion was sprayed onto the cores to obtain two different coatings 6.6% and 8.8% by weight in respect to core mass. During the coating process the tablet mass was controlled and thus the mass of coating was determined.

2.3. Analysis of Stability of the Active Substance in the Pharmaceutical Dosage Form of Example 2 in Different Atmospheres The effect of the protective coating was tested as described in Example 1.

TABLE 7

Increase of the assay of degradation products of atorvastatin in the tablets stored 14 days at 60° C. in nitrogen, air and oxygen atmosphere versus the tablets stored at 4° C.

| Pharmaceutical dosage form | Weight of coating in respect to core mass (%) | Weight of glycerol in respect to mass of Na CMC (%) | Increase of the assay of degradation products in % in different atmospheres | | |
|---|---|---|---|---|---|
| | | | Nitrogen | Air | Oxygen |
| Reference of Example 2 - uncoated tablet | 0 | 0 | 0.03 | 1.07 | 4.04 |
| Coated tablet of Example 2 | 6.6 | 10 | 0.08 | 0.08 | 0.06 |

TABLE 7-continued

Increase of the assay of degradation products of atorvastatin in the tablets stored 14 days at 60° C. in nitrogen, air and oxygen atmosphere versus the tablets stored at 4° C.

| Pharmaceutical dosage form | Weight of coating in respect to core mass (%) | Weight of glycerol in respect to mass of Na CMC (%) | Increase of the assay of degradation products in % in different atmospheres | | |
|---|---|---|---|---|---|
| | | | Nitrogen | Air | Oxygen |
| Coated tablet of Example 2 | 8.8 | 10 | 0.05 | 0.00 | 0.04 |

An increase of the degradation products of atorvastatin in the uncoated tablet in comparison to the coated tablet of Example 2 is approximately more than ten times greater for the samples in air atmosphere and more than sixty times greater for the samples in oxygen atmosphere. The coating of Example 2 effectively prevents ingress of oxygen to the tablet core and to the active substance thus preventing occurrence of degradation products of the active substance.

Example 3

Composition of One Coated Tablet 3.1. Tablet Core

TABLE 8

Composition of the core

| Ingredient | Mass (mg) |
|---|---|
| Atorvastatin (in the form of atorvastatin Ca) | 10.00 |
| Microcrystalline cellulose | 153.20 |
| Lactose monohydrate | 34.80 |
| Crosslinked carboxymethylcellulose | 19.20 |
| Hydroxypropyl cellulose | 2.00 |
| Polysorbate 80 | 2.60 |
| Magnesium ixide | 26.00 |
| Colloidal silicon dioxide | 1.20 |
| Magnesium stearate | 1.00 |

Preparation of Tablet Core

Atorvastatin, 53% of the total microcrystalline cellulose, lactose monohydrate, half of crosslinked carboxymethylcellulose and 11% of the total magnesium oxide were homogeneously mixed and granulated with a solution of hydroxypropyl cellulose and polysorbate in water. The granulate was dried in a fluid bed dryer and the sieved granulate was homogeneously mixed with the rest of microcrystalline cellulose, crosslinked carboxymethylcellulose and magnesium oxide, colloidal silicon dioxide and magnesium stearate. The homogeneous granulate was compressed into tablets, mass 250 mg, on a conventional tablet press.

3.2. Tablet Coating

TABLE 4

Composition of a coating

| Coating ingredients | Weight of coating in respect to core mass (%) and mass of ingredients in a coating (mg) | |
|---|---|---|
| | 6.6% | 8.7% |
| Sodium carboxymenthylcellulose | 14.00 mg | 18.64 mg |
| Glycerol | 2.80 mg | 3.73 mg |

Preparation of a Coating Dispersion and Coating of Tablet Cores

Sodium carboxymethylcellulose (Blanose CMC 7LF PH, Aqualon), (111.84 g) with viscosity 25 to 50 mPas and glycerol (22.38 g) while mixing were dissolved in water (2576.40 g). The resulting dispersion was sprayed onto the cores to obtain two different coatings 6% and 8% by weight in respect to core mass. During the coating process the tablet mass was controlled and thus the mass of coating was determined.

3.3. Analysis of Stability of the Active Substance in the Pharmaceutical Dosage Form of Example 3 in Different Atmospheres The effect of the protective coating was tested as described in Example 1.

TABLE 10

Increase of the assay of degradation products of atorvastatin in the tablets stored 14 days at 60° C. in nitrogen, air and oxygen atmosphere versus the tablets stored at 4° C.

| Pharmaceutical dosage form | Weight of coating in respect to core mass (%) | Weight of glycerol in respect to mass of Na CMC (%) | Increase of the assay of degradation products in % in different atmospheres | | |
|---|---|---|---|---|---|
| | | | Nitrogen | Air | Oxygen |
| Reference of Example 3 - uncoated tablet | 0 | 0 | 0.03 | 1.07 | 4.04 |
| Coated tablet of Example 3 | 6.6 | 20 | 0.05 | 0.06 | 0.03 |
| Coated tablet of Example 3 | 8.7 | 20 | 0.04 | 0.00 | 0.00 |

Similar to Example 2, an increase of the degradation products of atorvastatin in the uncoated tablet in comparison to the coated tablet of Example 3 is approximately more than ten times greater for the samples in air atmosphere and more than hundred times greater for the samples in oxygen atmosphere. The coating of Example 3 effectively prevents ingress of oxygen to the tablet core and to the active substance thus preventing occurrence of degradation products of the active substance.

Example 4

Composition of One Coated Tablet 4.1. Tablet Core

TABLE 11

Composition of the core

| Ingredient | Mass (mg) |
| --- | --- |
| Atorvastatin (in the form of atorvastatin Ca) | 10.00 |
| Microcrystalline cellulose | 153.20 |
| Lactose monohydrate | 34.80 |
| Crosslinked carboxymethylcellulose | 19.20 |
| Hydroxypropyl cellulose | 2.00 |
| Polysorbate 80 | 2.60 |

TABLE 11-continued

Composition of the core

| Ingredient | Mass (mg) |
| --- | --- |
| Magnesium oxide | 26.00 |
| Colloidal silicon dioxide | 1.20 |
| Magnesium stearate | 1.00 |

Preparation of Tablet Core

Atorvastatin, 53% of the total microcrystalline cellulose, lactose monohydrate, half of crosslinked carboxymethylcellulose and 11% of the total magnesium oxide were homogeneously mixed and granulated with a solution of hydroxypropyl cellulose and polysorbate in water. The granulate was dried in a fluid bed dryer and the sieved granulate was homogeneously mixed with the rest of microcrystalline cellulose, crosslinked carboxymethylcellulose and magnesium oxide, colloidal silicon dioxide and magnesium stearate. The homogeneous granulate was compressed into tablets, mass 250 mg, on a conventional tablet press.

4.2. Tablet Coating

TABLE 12

Composition of a coating

| Coating ingredients | Weight of coating in respect to core mass (%) and mass of ingredients in a coating (mg) | |
| --- | --- | --- |
| | 7.1% | 9.5% |
| Sodium carboxymenthylcellulose | 14.00 mg | 18.64 mg |
| Glycerol | 4.20 mg | 5.59 mg |

Preparation of a Coating Dispersion and Coating of Tablet Cores

Sodium carboxymethylcellulose (Blanose CMC 7LF PH, Aqualon), (111.84 g) with viscosity 25 to 50 mPas and glycerol (33.54 g) while mixing were dissolved in water (2576.40 g). The resulting dispersion was sprayed onto the cores to obtain different coatings 7.1% and 9.5% by weight in respect to core mass. During the coating process the tablet mass was controlled and thus the mass of coating was determined.

4.3. Analysis of Stability of the Active Substance in the Pharmaceutical Dosage Form of Example 4 in Different Atmospheres The effect of the protective coating was tested as described in Example 1.

TABLE 13

Increase of the assay of degradation products of atorvastatin in the tablets stored 14 days at 60° C. in nitrogen, air and oxygen atmosphere versus the tablets stored at 4° C.

| Pharmaceutical dosage form | Weight of coating in respect to core mass (%) | Weight of glycerol in respect to mass of Na CMC (%) | Increase of the assay of degradation products in % in different atmospheres | | |
| --- | --- | --- | --- | --- | --- |
| | | | Nitrogen | Air | Oxygen |
| Reference of Example 4 - uncoated tablet | 0 | 0 | 0.03 | 1.07 | 4.04 |
| Coated tablet of Example 4 | 7.1 | 30 | 0.05 | 0.00 | 0.07 |
| Coated tablet of Example 4 | 9.5 | 30 | 0.01 | 0.02 | 0.03 |

The increase of degradation products in air and in oxygen atmosphere are extremely low. The coating of Example 4 effectively prevents ingress of oxygen to the tablet core and to the active substance thus preventing occurrence of degradation products of the active substance similar to the Example 2 and 3.

Example 5

Composition of One Coated Tablet 5.1. Tablet Core

TABLE 14

Composition of the core

| Ingredient | Mass (mg) |
| --- | --- |
| Atorvastatin (in the form of atorvastatin Ca) | 40.00 |
| Sodium lauryl sulfate | 30.0 |
| ProSolv HD 90 | 160.00 |
| Pregelitinized corn starch | 3.75 |

TABLE 14-continued

Composition of the core

| Ingredient | Mass (mg) |
| --- | --- |
| Crosslinked carboxymethylcellulose | 12.50 |
| Magnesium stearate | 1.25 |
| Talc | 2.50 |

Preparation of Tablet Core

Atorvastatin Ca, ProSolv HD 90, sodium lauryl sulfate, pregelatinized corn starch and crosslinked carboxymethylcellulose were homogeneously mixed. Magnesium stearate and talc were added, homogeneously mixed and compressed into tablets, mass 250 mg, in a room with controlled low relative air humidity.

5.2. Tablet Coating

TABLE 15

Composition of a coating

| | Weight of coating in respect to core mass (%) and mass of ingredients in a coating (mg) | |
| --- | --- | --- |
| Coating ingredients | 6% | 8% |
| Sodium carboxymenthylcellulose | 12.275 mg | 16.363 mg |
| Glycerol | 1.225 mg | 1.637 mg |
| Titanium dioxide | 1.406 mg | 1.875 mg |
| Pigment yellow | 0.094 mg | 0.125 mg |

Preparation of a Coating Dispersion and Coating of Tablet Cores

Sodium carboxymethylcellulose (Blanose CMC 7LF PH, Aqualon), (98.178 g) with viscosity 25 to 50 mPas and glycerol (9.822 g) while mixing were dissolved in water (2230 g) and then while mixing a dispersion of coloring concentrate was added. A coloring concentrate was prepared by dispersing an aqueous dispersion of titanium dioxide (11.250 g) and pigment yellow (Sicopharm 10, BASF), (0.750 g). The resulting dispersion was sprayed onto the cores to obtain two different coatings 6% and 8% by weight in respect to core mass. During the coating process the tablet mass was controlled and thus the mass of coating was determined.

Example 6

Composition of One Coated Tablet 6.1. Tablet Core

TABLE 16

Composition of the core

| Ingredient | Mass (mg) |
| --- | --- |
| Atorvastatin (in the form of atorvastatin Ca) | 40.00 |
| Sodium lauryl sulfate | 30.0 |
| ProSolv SMCC 90 | 149.00 |
| $Na_3PO_4 \cdot 12H_2O$ | 11.00 |
| Pregelitinized corn starch | 3.75 |
| Crosslinked carboxymethylcellulose | 12.50 |
| Magnesium stearate | 1.25 |
| Talc | 2.50 |

Preparation of Tablet Core

A solution of $Na_3PO_4 \cdot 12H_2O$ was dispersed in the stream of warm air on ProSolv SMCC 90. The resulting granulate was dried and sieved. Atorvastatin, sodium lauryl sulfate, pregelatinized corn starch and crosslinked carboxymethylcellulose were added and then homogeneously mixed. Magnesium stearate and talc were added, homogeneously mixed and compressed into tablets, mass 250 mg, in a room with controlled low relative air humidity.

6.2. Tablet Coating

TABLE 17

Composition of a coating

| | Weight of coating in respect to core mass (%) and mass of ingredients in a coating (mg) | |
| --- | --- | --- |
| Coating ingredients | 6% | 8% |
| Sodium carboxymenthylcellulose | 12.275 mg | 16.363 mg |
| Glycerol | 1.225 mg | 1.637 mg |
| Titanium dioxide | 1.406 mg | 1.875 mg |
| Pigment yellow | 0.094 mg | 0.125 mg |

Preparation of a Coating Dispersion and Coating of Tablet Core

Sodium carboxymethylcellulose (Blanose CMC 7LF PH, Aqualon), (98.178 g) with viscosity 25 to 50 mPas and glycerol (9.822 g) while mixing were dissolved in water (2230 g) and then while mixing a dispersion of coloring concentrate was added. A coloring concentrate was prepared by dispersing an aqueous dispersion of titanium dioxide (11.250 g) and pigment yellow (Sicopharm 10, BASF), (0.750 g). The resulting dispersion was sprayed onto the cores to obtain two different coatings 6% and 8% by weight in respect to core mass. During the coating process the tablet mass was controlled and thus the mass of coating was determined.

Example 7

Composition of One Coated Tablet 7.1. Tablet Core

TABLE 16

Composition of the core

| Ingredient | Mass (mg) |
| --- | --- |
| Atorvastatin (in the form of atorvastatin Ca) | 40.00 |
| Sodium lauryl sulfate | 30.00 |
| ProSolv SMCC 90 | 110.00 |
| Na citrate dihydrate | 50.00 |
| Pregelitinized corn starch | 3.75 |
| Crosslinked carboxymethylcellulose | 12.50 |
| Magnesium stearate | 1.25 |
| Talc | 2.50 |

Preparation of Tablet Core

A solution of Na citrate dihydrate was dispersed in the stream of warm air on ProSolv SMCC 90. The resulting granulate was dried and sieved. Atorvastatin, sodium lauryl sulfate, pregelatinized corn starch and crosslinked carboxymethylcellulose were added and then homogeneously mixed. Magnesium stearate and talc were added, homogeneously mixed and compressed into tablets, mass 250 mg, in a room with controlled low relative air humidity.

7.2. Tablet Coating

TABLE 19

Composition of a coating

| Coating ingredients | Weight of coating in respect to core mass (%) and mass of ingredients in a coating (mg) | |
|---|---|---|
| | 6% | 8% |
| Sodium carboxymenthylcellulose | 12.275 mg | 16.363 mg |
| Glycerol | 1.225 mg | 1.637 mg |
| Titanium dioxide | 1.406 mg | 1.875 mg |
| Pigment yellow | 0.094 mg | 0.125 mg |

Preparation of a Coating Dispersion and Coating of Tablet Core

Sodium carboxymethylcellulose (Blanose CMC 7LF PH, Aqualon), (98.178 g) with viscosity 25 to 50 mPas and glycerol (9.822 g) while mixing were dissolved in water (2230 g) and then while mixing a dispersion of coloring concentrate was added. A coloring concentrate was prepared by dispersing an aqueous dispersion of titanium dioxide (11.250 g) and pigment yellow (Sicopharm 10, BASF), (0.750 g). The resulting dispersion was sprayed onto the cores to obtain two different coatings 6% and 8% by weight in respect to core mass. During the coating process the tablet mass was controlled and thus the mass of coating was determined.

Example 8

Composition of One Coated Tablet 8.1. Tablet Core

TABLE 20

Composition of the core

| Ingredient | Mass (mg) |
|---|---|
| Atorvastatin (in the form of atorvastatin Ca) | 40.00 |
| Sodium lauryl sulfate | 5.00 |
| ProSolv SMCC 90 | 139.00 |
| Pregelitinized corn starch | 3.00 |
| Crosslinked carboxymethylcellulose | 10.00 |
| Magnesium stearate | 1.00 |
| Talc | 2.00 |

Preparation of Tablet Core

A solution of sodium lauryl sulfate was dispersed in the stream of warm air on atorvastatin Ca. The resulting granulate was dried and sieved. ProSolv SMCC 90, pregelitinized corn starch and crosslinked carboxymethylcellulose were homogeneously mixed. Magnesium stearate and talc were added, homogeneously mixed and compressed into tablets, mass 200 mg.

8.2. Tablet Coating

TABLE 21

Composition of a coating

| Coating ingredients | Weight of a coating in respect to core mass (%) and ingredient mass in a core (mg) 8% |
|---|---|
| Sodium carboxymethylcellulose | 14.90 mg |
| Glycerol | 1.50 mg |

Preparation of a Coating Dispersion and Coating of Tablet Cores

Sodium carboxymethylcellulose (Blanose CMC 7LF PH, Aqualon), (109.00 g) with viscosity 25 to 50 mPas and glycerol (11.00 g) while mixing were dissolved in water (2513.60 g). The resulting dispersion was sprayed onto the cores to obtain an 8% coating by weight in respect to core mass. During the coating process the tablet mass was controlled and thus the mass of coating was determined.

8.3. Determination of the pH Value of Tablets

The pH value of the tablet of Example 8, determined potentiometrically, was 6.7. By the same procedure, the pH value of the mixture atorvastatin Ca and ProSolv SMCC 90 (mixture in a ratio equivalent to their ratio by weight in a tablet) was determined, and it was 7.93.

The pH values of the tablet and the mixture of the active substance and the filler ProSolvSMOC 90 were determined in 20 ml aqueous dispersion of 1 tablet with the assay of 40 mg atorvastatin Ca, that is, in the dispersion of the mixture of the active substance and the filler ProSolv SMCC 90 in the amount present in said tablet. The pH value was determined on analytical equipment 720 KFS Titrino Methrom using combined micro pH electrode Methrom 6.0204.100 pH 14/0 70° C.

8.4 Analysis of Stability of the Active Substance in the Pharmaceutical Dosage Form of Example 8 in Different Atmospheres The influence of water/humidity and pharmaceutical excipients on occurrence of degradation products (lactone and oxidative degradation products) was assessed by testing coated tablets in the packages (HDPE plastic bottles) with different desiccants (without desiccant, silica gel, molecular sieves). Coated tablets were stored for 1 month under the conditions 40/75 (40° C.±2° C., 75% RH±5%). The assay of degradation products of atorvastatin (lactone and oxidative degradation products) was determined by liquid chromatography. As reference sample the tablets stored in a refrigerator (2-8° C.) were analyzed. The moisture content in the tablets was measured gravimetrically by determining loss on drying (LOD).

TABLE 22

Increase in the assay of degradation products of atorvastatin (lactone) in the coated tablets of said invention, stored 1 month under the conditions 40/75 (40° C. ± 2° C., 75% RH ± 5%)

| Desiccant | LOD* (%) | Storage conditions | Increase of lactone assay in % to reference sample |
|---|---|---|---|
| Reference sample | 5.08 | Refrigerator, 1 month (reference) | |
| without desiccant | 5.17 | 40/75, 1 month | 0.21 |
| 2 g silica gel | 3.49 | 40/75, 1 month | 0.05 |

TABLE 22-continued

Increase in the assay of degradation products of atorvastatin (lactone) in the coated tablets of said invention, stored 1 month under the conditions 40/75 (40° C. ± 2° C., 75% RH ± 5%)

| Desiccant | LOD* (%) | Storage conditions | Increase of lactone assay in % to reference sample |
|---|---|---|---|
| 4 g silica gel | 2.73 | 40/75, 1 month | 0.04 |
| 2 g molecular sieves | 1.99 | 40/75, 1 month | 0.03 |
| 4 g molecular sieves | 1.55 | 40/75, 1 month | 0.03 |
| 2 g silica gel + 2 g molecular sieves | 1.73 | 40/75, 1 month | 0.03 |

LOD*-loss on drying

After one month of testing under the condition of accelerated stability it was observed that due to smaller percent of moisture in the tablets with added desiccant, lactone in said tablets was formed in a considerably smaller percent (level 0.05%) compared to the tablets with no added desiccant (level 0.22%). Under the determined level of humidity, differences in the percentage of formed lactone in the tablets, i.e. below 3.50% of moisture estimated as loss on drying were not significant.

TABLE 23

Increase in the assay of degradation products of atorvastatin (oxidative degradation products in the coated tablets of said invention, stored 1 month under the conditions 40/75 (40° C. ± 2° C., 75% RH ± 5%)

| | | | Increase in assay of oxidative degradation products in % to reference sample | |
|---|---|---|---|---|
| Desiccant | LOD* (%) | Storage conditions | Uncoated tablets | Coated tablets according to Example 8 |
| Reference sample | 5.08 | Refrigerator, 1 month (reference) | | |
| without desiccant | 5.17 | 40/75, 1 month | 0.20 | 0.14 |
| 2 g silica gel | 3.49 | 40/75, 1 month | 0.42 | 0.12 |
| 4 g silica gel | 2.73 | 40/75, 1 month | 0.34 | 0.12 |
| 2 g molecular sieves | 1.99 | 40/75, 1 month | 0.43 | 0.15 |
| 4 g molecular sieves | 1.55 | 40/75, 1 month | 0.38 | 0.13 |
| 2 g silica gel + 2 g molecular sieves | 1.73 | 40/75, 1 month | 0.36 | 0.11 |

LOD*-loss on drying

After one month of testing under the condition of accelerated stability the increase of degradation products of atorvastatin (oxidative degradation products) in the coated tablet of said invention was significantly smaller than in the uncoated tablet.

Example 9

Composition of One Coated Tablet 9.1. Tablet Core

TABLE 24

Composition of the core

| Ingredient | Mass (mg) |
|---|---|
| Atorvastatin (in the form of atorvastatin Ca) | 20.00 |
| Microcrystalline cellulose | 143.20 |
| Lactose monohydrate | 34.80 |

TABLE 24-continued

Composition of the core

| Ingredient | Mass (mg) |
|---|---|
| Crosslinked carboxymethylcellulose | 19.20 |
| Hydroxypropyl cellulose | 2.00 |
| Polysorbate 80 | 2.60 |
| Magnesium oxide | 26.00 |
| Colloidal silicon dioxide | 1.20 |
| Magnesium stearate | 1.00 |

Preparation of Tablet Core

Atorvastatin, a part of microcrystalline cellulose, lactose monohydrate, a part of crosslinked carboxymethylcellulose and a part of magnesium oxide were homogeneously mixed and granulated with a solution of hydroxypropyl cellulose and polysorbate in water. The granulate was dried in a fluid bed dryer and the sieved granulate was homogeneously mixed with a part of microcrystalline cellulose, a part of crosslinked carboxymethylcellulose, a part of magnesium oxide, colloidal silicon dioxide and magnesium stearate. The homogeneous granulate was compressed into tablets, mass 250 mg, on a conventional tablet press.

9.2. Tablet Coating

TABLE 25

Composition of a coating

| | Weight of coating in respect to core mass (%) and mass of ingredients in a coat (mg) | |
|---|---|---|
| Coating ingredients | 6% | 8% |
| Sodium carboxymenthylcellulose | 9,800 mg | 14,350 mg |
| Polivinyl alcohol | 5,600 mg | 6,150 mg |

Preparation of a Coating Dispersion and Coating of Tablet Cores

Polyvinyl alcohol (Mowiol 28-99, Fluca) (36,900 g) was stirred into the water at room temperature. The mixture was then heated to 90° C., mixed for 5 minutes and then cooled to room temperature. Then the Sodium carboxymethylcellulose (Blanose CMC 7LF PH, Aqualon), (86,100 g) with viscosity 25 to 50 mPas while mixing was added and stirred for 60 minutes. The resulting dispersion was sprayed onto the cores to obtain different coatings 6% and 8% by weight in respect to core mass. During the coating process the tablet mass was controlled and thus the mass of coating was determined.

Example 10

Composition of One Coated Tablet 10.1. Tablet Core

TABLE 26

Composition of the core

| Ingredient | Mass (mg) |
|---|---|
| Atorvastatin (in the form of atorvastatin Ca) | 40.00 |
| Sodium lauryl sulfate | 10.00 |
| Pigment yellow | 0.72 |

TABLE 26-continued

Composition of the core

| Ingredient | Mass (mg) |
|---|---|
| Tris | 5.00 |
| ProSolv HD 90 | 389.48 |
| Sodium Starch Glycolate | 28.80 |
| Magnesium stearate | 1.20 |
| Talc | 4.80 |

Preparation of Tablet Core

First, a triturate of pigment yellow and a part of ProSolv was prepared and then homogenized with the rest of ProSolv. Atorvastatin, Tris, sodium lauryl sulfate, sodium starch glycolate were added and homogeneously mixed, Magnesium stearate and talc were added, homogeneously mixed and compressed into tablets, mass 480 mg.

10.2. Tablet Coating

TABLE 27

Composition of a coating

| Coating ingredients | Mass of ingredients in the coating (mg) |
|---|---|
| Sodium carboxymethylcellulose | 31.700 mg |
| Glycerol | 6.300 mg |

Preparation of a Coating Dispersion and Coating of Tablet Core

Sodium carboxymethylcellulose (Blanose CMC 7LF PH, Aqualon), (85.59 g) with viscosity 25 to 50 mPas and glycerol (Cognis), (17.01 g) while mixing were dissolved in water (1466.10 g). The resulting dispersion was sprayed onto the cores to an 8% coating by weight in respect to core mass. During the coating process the tablet mass was controlled and thus the mass of coating was determined.

10.3. Disintegration of Coated Tablets

Disintegration of coated tablets was determined with the disintegration test apparatus (Charles Isci, without discs) in 0.01 M HCl at 37° C. Disintegration was tested on 12 tablets. The average disintegration time of 11 tablets is 419.7 s. One of the tablets was not disintegrated even after 15 minutes. The time, when water perfuses through coating is decisive for coated tablet disintegration.

10.4. Analysis of Stability of the Active Substance in the Pharmaceutical Dosage Form of Example 10 in Different Atmospheres The effect of the protective coating was tested as described in Example 1.

TABLE 28

Increase of the assay of degradation products of atorvastatin in the tablets stored 14 days at 60° C. in nitrogen, air and oxygen atmosphere versus the tablets stored at 4° C.

| Pharmaceutical formulation | Weight of coating in respect to core mass (%) | Weight of glycerol in respect to mass of Na CMC (%) | Increase of the assay of degradation products in % in different atmospheres | | |
|---|---|---|---|---|---|
| | | | Nitrogen | Air | Oxygen |
| Reference example - uncoated tablet | 0 | 0 | 0.02 | 1.48 | 4.72 |
| Coated tablet of Example 10 | 8 | 20 | 0.22 | 0.39 | 0.47 |

The increase of the degradation products of atorvastatin in the uncoated tablet in comparison to the coated tablet of Example 10 is approximately more than three times greater for the samples in air atmosphere and about ten times greater for the samples in oxygen atmosphere. The coating of Example 10 prevents ingress of oxygen to the tablet core and to the active substance thus preventing occurrence of degradation products of the active substance.

Example 11

Composition of One Coated Tablet 11.1. Tablet Core

Tablet cores from Example 1 were used.

11.2. Tablet Coating

TABLE 29

Composition of a coating

| Coating ingredients | Mass of ingredients in the coating (mg) |
|---|---|
| Sodium carboxymethylcellulose | 31.700 mg |
| Glycerol | 6.300 mg |
| Tris | 3.000 mg |

Preparation of a Coating Dispersion and Coating of Tablet Core

Sodium carboxymethylcellulose (Blanose CMC 7LF PH, Aqualon), (85.59 g) with viscosity 25 to 50 mPas, glycerol (Cognis), (17.01 g) and Tris (PharmaGrade, AppliChem), (8.10 g) while mixing were dissolved in water (1466.10 g). The resulting dispersion was sprayed onto the cores to an 8% coating by weight in respect to core mass. During the coating process the tablet mass was controlled and thus the mass of coating was determined.

11.3. Disintegration of Coated Tablets

Disintegration of coated tablets was determined with the disintegration test apparatus (Charles Isci, without discs) in 0.01 M HCl at 37° C. Disintegration was tested on 12 tablets. The average disintegration time is 284.7 s. Therefore, disintegration time of coated tablets is significantly faster with the addition of alkalizing substance (Tris) in coating.

11.4. Analysis of Stability of the Active Substance in the Pharmaceutical Dosage Form of Example 11 in Different Atmospheres The effect of the protective coating was tested as described in Example 1.

TABLE 30

Increase of the assay of degradation products of atorvastatin in the tablets stored 14 days at 60° C. in nitrogen, air and oxygen atmosphere versus the tablets stored at 4° C.

| Pharmaceutical formulation | Weight of coating in respect to core mass (%) | Weight of glycerol in respect to mass of Na CMC (%) | Increase of the assay of degradation products in % in different atmospheres | | |
|---|---|---|---|---|---|
| | | | Nitrogen | Air | Oxygen |
| Reference example - uncoated tablet | 0 | 0 | 0.02 | 1.48 | 4.72 |
| Coated tablet of Example 11 | 8 | 20 | 0.22 | 0.21 | 0.24 |

The increase of the degradation products of atorvastatin in the uncoated tablet in comparison to the coated tablet of Example 11 is approximately seven times greater for the samples in air atmosphere and about twenty times greater for the samples in oxygen atmosphere. The coating of Example 11 prevents ingress of oxygen to the tablet core and to the active substance thus preventing occurrence of degradation products of the active substance.

Example 12

Composition of One Coated Tablet 12.1. Tablet Core

Tablet cores from Example 1 were used.

12.2. Tablet Coating

TABLE 31

Composition of a coating

| Coating ingredients | Mass of ingredients in the coating (mg) |
|---|---|
| Sodium carboxymethylcellulose | 31.700 mg |
| Glycerol | 6.300 mg |
| Tris | 3.000 mg |
| Sodium lauryl sulfate | 1.500 mg |

Preparation of a Coating Dispersion and Coating of Tablet Core

Sodium carboxymethylcellulose (Blanose CMC 7LF PH, Aqualon), (85.59 g) with viscosity 25 to 50 mPas, glycerol (Cognis), (17.01 g), Tris (PharmaGrade, AppliChem), (8.10 g) and sodium lauryl sulfate (Texapon K12, Cognis), (4.05 g) while mixing were dissolved in water (1466.10 g). The resulting dispersion was sprayed onto the cores to an 8% coating by weight in respect to core mass. During the coating process the tablet mass was controlled and thus the mass of coating was determined.

12.3. Disintegration of Coated Tablets

Disintegration of coated tablets was determined with the disintegration test apparatus (Charles Isci, without discs) in 0.01 M HCl at 37° C. Disintegration was tested on 12 tablets. The average disintegration time is 287.7 s. Therefore, disintegration time of coated tablets is significantly faster with the addition of alkalizing substance (Tris) and surfactant (sodium lauryl sulfate) in coating.

12.4. Analysis of Stability of the Active Substance in the Pharmaceutical Dosage Form of Example 12 in Different Atmospheres The effect of the protective coating was tested as described in Example 1.

TABLE 32

Increase of the assay of degradation products of atorvastatin in the tablets stored 14 days at 60° C. in nitrogen, air and oxygen atmosphere versus the tablets stored at 4° C.

| Pharmaceutical formulation | Weight of coating in respect to core mass (%) | Weight of glycerol in respect to mass of Na CMC (%) | Increase of the assay of degradation products in % in different atmospheres | | |
|---|---|---|---|---|---|
| | | | Nitrogen | Air | Oxygen |
| Reference example 12 uncoated tablet | 0 | 0 | 0.02 | 1.48 | 4.72 |
| Coated tablet of Example 12 | 8 | 20 | 0.23 | 0.23 | 0.28 |

The increase of the degradation products of atorvastatin in the uncoated tablet in comparison to the coated tablet of Example 12 is approximately six times greater for the samples in air atmosphere and about seventeen times greater for the samples in oxygen atmosphere. The coating of Example 12 prevents ingress of oxygen to the tablet core and to the active substance thus preventing occurrence of degradation products of the active substance.

Example 13

Composition of One Coated Tablet 13.1. Tablet Core

TABLE 33

Composition of the core

| Ingredient | Mass (mg) |
|---|---|
| Atorvastatin (in the form of atorvastatin Ca) | 40.00 |
| Sodium lauryl sulfate | 7.00 |
| Pigment yellow | 0.72 |
| Tris | 5.00 |
| ProSolv HD 90 | 385.28 |
| Sodium Starch Glycolate | 28.80 |
| Pregelatinized corn starch | 7.20 |
| Magnesium stearate | 1.20 |
| Talc | 4.80 |

Preparation of Tablet Core

First, a triturate of pigment yellow and a part of ProSolv was prepared and then homogenized with the rest of ProSolv. Atorvastatin, Tris, sodium lauryl sulfate, pregelatinized corn starch, sodium starch glycolate were added and homogeneously mixed. Magnesium stearate and talc were added, homogeneously mixed and compressed into tablets, mass 480 mg.

13.2. Tablet Coating

TABLE 34

Composition of a coating

| Coating ingredients | Mass of ingredients in the coating (mg) |
|---|---|
| Sodium carboxymethylcellulose | 35.700 mg |
| Glycerol | 7.100 mg |

TABLE 34-continued

Composition of a coating

| Coating ingredients | Mass of ingredients in the coating (mg) |
|---|---|
| Tris | 3.000 mg |
| Sodium lauryl sulfate | 1.000 mg |

Preparation of a Coating Dispersion and Coating of Tablet Core

Sodium carboxymethylcellulose (Blanose CMC 7LF PH, Aqualon), (187.425 g) with viscosity 25 to 50 mPas, glycerol (Cognis), (37.275 g), Tris (PharmaGrade, AppliChem), (15.750 g) and sodium lauryl sulfate (Texapon K12, Cognis), (5.250 g) while mixing were dissolved in water (3223.500 g). The resulting dispersion was sprayed onto the cores to an 9% coating by weight in respect to core mass. During the coating process the tablet mass was controlled and thus the mass of coating was determined.

13.3. Disintegration of Coated Tablets

Disintegration of coated tablets was determined with the disintegration test apparatus (Charles Isci, without discs) in 0.01 M HCl at 37° C. Disintegration was tested on 24 tablets. The average disintegration time is 387.4 s.

13.4. Analysis of Stability of the Active Substance in the Pharmaceutical Dosage Form of Example 13 in Different Atmospheres The effect of the protective coating was tested as described in Example 1.

TABLE 35

Increase of the assay of degradation products of atorvastatin in the tablets stored 14 days at 60° C. in nitrogen, air and oxygen atmosphere versus the tablets stored at 4° C.

| Pharmaceutical formulation | Weight of coating in respect to core mass (%) | Weight of glycerol in respect to mass of Na CMC (%) | Increase of the assay of degradation products in % in different atmospheres | | |
|---|---|---|---|---|---|
| | | | Nitrogen | Air | Oxygen |
| Reference example - uncoated tablet | 0 | 0 | 0.00 | 1.28 | 5.27 |
| Coated tablet of Example 13 | 9 | 20 | 0.26 | 0.23 | 0.27 |

The increase of the degradation products of atorvastatin in the uncoated tablet in comparison to the coated tablet of Example 13 is approximately five times greater for the samples in air atmosphere and about nineteen times greater for the samples in oxygen atmosphere. The coating of Example 13 prevents ingress of oxygen to the tablet core and to the active substance thus preventing occurrence of degradation products of the active substance.

Example 14

Tablet with Coated Active Substance

TABLE 36

Composition of a tablet with coated active substance

| Ingredient | Mass (mg) |
|---|---|
| Atorvastatin (in the form of atorvastatin Ca) | 40.00 |
| Sodium carboxymethylcellulose | 3.20 |

TABLE 36-continued

Composition of a tablet with coated active substance

| Ingredient | Mass (mg) |
|---|---|
| Glycerol | 0.32 |
| Sodium lauryl sulfate | 30.00 |
| Cellactose 80 | 133.48 |
| Granulated mannitol | 30.00 |
| Crosslinked carboxymethylcellulose | 10.00 |
| Magnesium stearate | 1.00 |
| Talc | 2.00 |

Preparation of Tablet with Coated Active Substance

A colloidal solution of sodium carboxymethylcellulose and glycerol was dispersed in the stream of warm air on atorvastatin Ca. The resulting coated active substance was dried and sieved. Cellastose 80, sodium lauryl sulfate, granulated mannitol and crosslinked carboxymethylcellulose were added and then homogeneously mixed. Magnesium stearate and talc were added, homogeneously mixed and compressed into tablets, mass 250 mg.

The invention claimed is:

1. A composition comprising at least one particle enclosed in a coating, wherein said particle comprises an active ingredient which is a HMG-CoA reductase inhibitor, said active ingredient being susceptible to degradation upon exposure to oxidation or humidity or both, and a coating, wherein
    said coating comprises an admixture of
    (a) a film-forming substance selected from the group consisting of polyvinyl alcohol, sodium carboxymethylcellulose, hydroxyethylcellulose and combinations thereof and
    (b) at least one pharmaceutical excipient selected from the group consisting of a buffering agent, an alkalizing agent and a surface active agent wherein the film-forming substance is present in concentrations of 60-95% of the amount of the solids in the coating,
    said coating having a thickness within the range of 5 µm to 200 µm and said coating confers stability to the active ingredient against oxidation or humidity or both, and said coating enabling the release of the active substance in all parts of the gastrointestinal tract, regardless of the environmental pH value.

2. The composition according to claim 1 wherein the HMG-CoA reductase inhibitor is at least one selected from the group consisting of atorvastatin, fluvastatin, lovastatin, mevastatin, pravastatin, rosuvastatin and simvastatin.

3. The composition according to claim 1 wherein the coating comprises a film-forming substance which is polyvinyl alcohol.

4. The composition according to claim 1 wherein the coating comprises a film-forming substance which is sodium carboxymethylcellulose.

5. The composition according to claim 1 wherein the coating further comprises a film-forming substance which is hydroxyethylcellulose.

6. The composition according to claim 1 wherein the coating further comprises a pharmaceutical excipient selected from the group consisting of a plasticizer, viscosity-increasing agent of a coating dispersion, filler, lubricant and colorant.

7. The composition according to claim 1 wherein the composition has a water content less than 5 weight percent, based on the total weight of the composition.

8. A composition comprising at least one particle enclosed in a coating, wherein said particle comprises an active ingredient which is a HMG-CoA reductase inhibitor, said active ingredient being susceptible to degradation upon exposure to oxidation or humidity or both, and a coating, wherein
    said coating comprises an admixture of
    (a) a film-forming substance selected from the group consisting of carboxymethylcellulose, hydroxyethylcellulose and combinations thereof and
    (b) at least one pharmaceutical excipient selected from the group consisting of a buffering agent, an alkalizing agent and a surface active agent wherein the film-forming substance is present in concentrations of 60-95% of the amount of the solids in the coating,
    said coating having a thickness within the range of 5 µm to 200 µm and said coating confers stability to the active ingredient against oxidation or humidity or both, and said coating enabling the release of the active substance in all parts of the gastrointestinal tract, regardless of the environmental pH value.

9. The composition according to claim 8 wherein the HMG-CoA reductase inhibitor is at least one selected from the group consisting of atorvastatin, fluvastatin, lovastatin, mevastatin, pravastatin, rosuvastatin and simvastatin.

10. The composition according to claim 8 wherein the coating comprises a film-forming substance which is sodium carboxymethylcellulose.

11. The composition according to claim 8 wherein the coating comprises a film-forming substance which is hydroxyethylcellulose.

12. A composition comprising at least one particle enclosed in a coating, wherein said particle comprises an active ingredient which is a HMG-CoA reductase inhibitor, said active ingredient being susceptible to degradation upon exposure to oxidation or humidity or both, and a coating, wherein said coating comprises an admixture of sodium carboxymethylcellulose and tromethamine, wherein the film-forming substance is present in concentrations of 60-95% of the amount of the solids in the coating, said coating having a thickness within the range of 5 µm to 200 µm and said coating confers stability to the active ingredient against oxidation or humidity or both, and said coating enabling the release of the active substance in all parts of the gastrointestinal tract, regardless of the environmental pH value.

13. A composition comprising one or more particles enclosed in a coating, wherein said particles comprise an active ingredient which is atorvastatin calcium, said active ingredient being susceptible to degradation upon exposure to oxidation or humidity or both, and a coating, wherein said coating comprises an admixture of a film-forming substance selected from the group consisting of polyvinyl alcohol, sodium carboxymethylcellulose, hydroxyethylcellulose and combinations thereof wherein the film-forming substance is present in concentrations of 60-95% of the amount of the solids in the coating, said coating having a thickness within the range of 5 µm to 200 µm and said coating confers stability to the active ingredient against oxidation or humidity or both, and said coating enabling the release of the active substance in all parts of the gastrointestinal tract, regardless of the environmental pH value.

14. The composition according to claim 13 wherein the coating comprises a film-forming substance which is polyvinyl alcohol.

15. The composition according to claim 13 wherein the coating comprises a film-forming substance which is sodium carboxymethylcellulose.

16. The composition according to claim 13 wherein the coating comprises a film-forming substance which is hydroxyethylcellulose.

17. The composition according to claim 13 wherein the coating further comprises a pharmaceutical excipient selected from the group consisting of a buffering agent, an alkalizing agent and a surface active agent.

18. The composition according to claim 13 wherein the coating further comprises a pharmaceutical excipient selected from the group consisting of a plasticizer, viscosity-increasing agent of a coating dispersion, filler, lubricant and colorant.

19. The composition according to claim 13 wherein the composition has a water content less than 5 weight percent, based on the total weight of the composition.

20. A composition comprising at least one particle enclosed in a coating, wherein said particle comprises an active ingredient which is a HMG-CoA reductase inhibitor, said active ingredient being susceptible to degradation upon exposure to oxidation or humidity or both, and a coating, wherein said coating comprises (a) a film-forming substance selected from the group consisting of polyvinyl alcohol, sodium carboxymethylcellulose, hydroxyethylcellulose and combinations thereof and (b) at least one pharmaceutical excipient selected from the group consisting of a buffering agent, an alkalizing agent and a surface active agent wherein the film-forming substance is present in concentrations of 60-95% of the amount of the solids in the coating, said coating having a thickness within the range of 5 μm to 200 μm and said coating confers stability to the active ingredient against oxidation or humidity or both, and said coating enabling the release of the active substance in all parts of the gastrointestinal tract, regardless of the environmental pH value.

* * * * *